US010568568B2

(12) United States Patent
Bhatnagar et al.

(10) Patent No.: US 10,568,568 B2
(45) Date of Patent: Feb. 25, 2020

(54) METHODS FOR IMMUNE GLOBULIN ADMINISTRATION

(71) Applicant: Capnia, Inc., Redwood City, CA (US)

(72) Inventors: Anish Bhatnagar, Redwood City, CA (US); Anthony D. Wondka, San Ramon, CA (US)

(73) Assignee: CAPNIA, INC., Foster City, CA (US)

( * ) Notice: Subject to any disclaimer, the term of this patent is extended or adjusted under 35 U.S.C. 154(b) by 164 days.

(21) Appl. No.: 14/838,241

(22) Filed: Aug. 27, 2015

(65) Prior Publication Data
US 2016/0060355 A1 Mar. 3, 2016

Related U.S. Application Data

(60) Provisional application No. 62/042,762, filed on Aug. 27, 2014.

(51) Int. Cl.
*A61B 5/00* (2006.01)
*G01N 33/497* (2006.01)

(52) U.S. Cl.
CPC ......... *A61B 5/4848* (2013.01); *G01N 33/497* (2013.01); *G01N 2033/4975* (2013.01)

(58) Field of Classification Search
CPC ..... A61B 5/082; A61B 5/4839; A61B 5/4848; G01N 2033/4975; G01N 33/497
See application file for complete search history.

(56) References Cited

U.S. PATENT DOCUMENTS

| | | | |
|---|---|---|---|
| 3,306,283 A | 2/1967 | Arp |
| 3,343,529 A | 9/1967 | Miller et al. |
| 3,858,573 A | 1/1975 | Ryan et al. |
| 3,910,261 A | 10/1975 | Ragsdale et al. |
| 4,082,734 A | 4/1978 | Stephan |
| 4,619,269 A | 10/1986 | Cutler et al. |
| 5,003,985 A | 4/1991 | White et al. |
| 5,069,220 A | 12/1991 | Casparie et al. |
| 5,072,737 A | 12/1991 | Goulding |
| 5,285,794 A | 2/1994 | Lynch |
| 5,293,875 A | 3/1994 | Stone |
| 5,361,772 A | 11/1994 | Murnick et al. |
| 5,383,469 A | 1/1995 | Vreman et al. |
| 5,573,005 A | 11/1996 | Ueda et al. |
| 5,924,995 A | 7/1999 | Klein et al. |

(Continued)

FOREIGN PATENT DOCUMENTS

EP 0 892 926 B2 12/2006
EP 2293056 A2 3/2011

(Continued)

OTHER PUBLICATIONS

Molloy et al., "Are carbon dioxide detectors useful in neonates?" Arch Dis Child Fetal Neonatal Ed (2006) 91:F295-F298.

(Continued)

*Primary Examiner* — Brandy S Lee
(74) *Attorney, Agent, or Firm* — Cooley LLP

(57) ABSTRACT

Methods for administering immune globulin and devices for use thereof. The methods may generally include measuring a patient's hemolysis levels and determining whether the patient is suitable for immune globulin treatment, determining whether immune globulin treatment should be continued, and/or determining if the dose needs to be changed.

2 Claims, 2 Drawing Sheets

(56) References Cited

U.S. PATENT DOCUMENTS

| | | | |
|---|---|---|---|
| 5,971,934 | A | 10/1999 | Scherer et al. |
| 6,010,459 | A | 1/2000 | Silkoff et al. |
| 6,251,082 | B1 | 6/2001 | Rayburn |
| 6,355,245 | B1 | 3/2002 | Evans et al. |
| 6,428,483 | B1 | 8/2002 | Carlebach |
| 6,544,190 | B1 | 4/2003 | Smits et al. |
| 6,582,376 | B2 | 6/2003 | Baghdassarian |
| 6,620,107 | B2 | 9/2003 | Payne et al. |
| 6,733,463 | B2 | 5/2004 | Moilanen et al. |
| 6,739,335 | B1 | 5/2004 | Rapport et al. |
| 6,799,575 | B1 | 10/2004 | Carter |
| 7,063,667 | B1 | 6/2006 | Ben-Oren et al. |
| 7,191,000 | B2 | 3/2007 | Zhu et al. |
| 7,223,244 | B1 | 5/2007 | Koh |
| 8,021,308 | B2 | 9/2011 | Capnia |
| 8,251,914 | B2 | 8/2012 | Daniels et al. |
| 8,485,984 | B2 | 7/2013 | Giron et al. |
| 8,679,029 | B2 | 3/2014 | Krauss et al. |
| 2001/0037070 | A1 | 11/2001 | Cranley et al. |
| 2002/0151814 | A1 | 10/2002 | Payne et al. |
| 2003/0008407 | A1 | 1/2003 | Fu |
| 2006/0195040 | A1 | 8/2006 | Nason et al. |
| 2006/0241507 | A1 | 10/2006 | Carlson et al. |
| 2007/0173731 | A1 | 7/2007 | Meka et al. |
| 2008/0009762 | A1 | 1/2008 | Hampton et al. |
| 2008/0071209 | A1 | 3/2008 | Moubayed et al. |
| 2008/0119753 | A1 | 5/2008 | Ricciardelli et al. |
| 2008/0121230 | A1 | 5/2008 | Cortez et al. |
| 2011/0004108 | A1 | 1/2011 | Peyton |
| 2011/0021942 | A1 | 1/2011 | Choe et al. |
| 2011/0066060 | A1 | 3/2011 | Von Bahr et al. |
| 2011/0318340 | A1* | 12/2011 | Collin et al. ........... C07K 16/00 424/133.1 |
| 2012/0055481 | A1 | 3/2012 | Orr et al. |
| 2012/0215125 | A1 | 8/2012 | Orr et al. |
| 2012/0247471 | A1 | 10/2012 | Masic et al. |
| 2013/0165806 | A1 | 6/2013 | Wondka et al. |
| 2014/0328856 | A1* | 11/2014 | Gelmont ................ C07K 16/18 424/152.1 |

FOREIGN PATENT DOCUMENTS

| | | |
|---|---|---|
| EP | 1850748 B1 | 8/2011 |
| WO | WO-2012/053910 A1 | 4/2012 |
| WO | WO-2012/059768 | 5/2012 |
| WO | WO-2012/076614 | 6/2012 |

OTHER PUBLICATIONS

Elalfy, M.S. et al. (2011). "Early intravenous immunoglobin (two-dose regimen) in the management of severe Rh hemolytic disease of newborn—a prospective randomized controlled trial," *Eur. J. Pediatr.* 170:461-467.

Herschel, M. et al. (2002). "Evaluation of the direct antiglobulin (Coombs') test for identifying newborns at risk for hemolysis as determined by end-tidal carbon monoxide concentration (ETCOc); and comparison of the Coombs' test with ETCOc for detecting significant jaundice," *J. Perinat.* 22:341-347.

Medtronic Capnography brochure MIN 3012492-001/CAT 21300-001569, 6 total pages.

International Search Report dated Dec. 28, 2015, for PCT Application No. PCT/US2015/47296, filed on Aug. 27, 2015, by Bhatnagar, Wondka and O'Sullivan, titled "Methods for Immune Globulin Administration," 4 pages.

International Search Report and Written Opinion dated May 13, 2013, for PCT Application No. PCT/US2012/71085, filed on Dec. 20, 2012, by Wondka, Bhatnagar and O'Sullivan, titled "Database for Correction of Collection and Analysis of Exhaled Gas With Breathing Parameter Frequency Compensation," 10 pages.

International Search Report and Written Opinion dated Apr. 15, 2014, for PCT Application No. PCT/US2014/10746, filed on Jan. 8, 2014, by Wondka, Bhatnagar, Gilbert and O'Sullivan, titled "Breath Selection for Analysis," 8 pages.

International Search Report and Written Opinion dated Apr. 30, 2014, for PCT Application No. PCT/US2014/016105, filed on Feb. 12, 2014, by Causevic, Wondka, Bhatnagar and O'Sullivan, titled "Sampling and Storage Registry Device for Breath Gas Analysis," 7 pages.

International Search Report and Written Opinion dated Dec. 18, 2014, for PCT Application No. PCT/US2014/053567, filed on Aug. 29, 2014, by De la Serna, Wondka, Blante and O'Sullivan, titled "Columnar Flow Gas Sampling and Measurement System," 7 pages.

International Search Report and Written Opinion dated Dec. 24, 2014, for PCT Application No. PCT/US2014/53572, filed on Aug. 29, 2014, by Wondka, Bhatnagar, De la Serna and O'Sullivan, titled "Neonatal Carbon Dioxide Measurement System," 7 pages.

International Search Report and Written Opinion dated Feb. 17, 2015, for PCT Application No. PCT/US2014/53569, filed on Aug. 29, 2014, by Bhatnagar, Wondka and O'Sullivan, titled "Universal Breath Analysis Sampling Device," 11 pages.

Written Opinion of the International Searching Authority dated Dec. 28, 2015, for PCT Application No. PCT/US2015/47296, filed on Aug. 27, 2015, by Bhatnagar, Wondka and O'Sullivan, titled "Methods for Immune Globulin Administration," 8 pages.

\* cited by examiner

METHODS FOR IMMUNE GLOBULIN ADMINISTRATION

CROSS-REFERENCE TO RELATED APPLICATION

This application claims the benefit of U.S. Provisional Application No. 62/042,762, filed Aug. 27, 2014, the content of which is incorporated herein in its entirety.

FIELD

Described herein are methods for administering immune globulin and devices for use thereof. The methods may generally include measuring a patient's hemolysis levels and determining whether the patient is suitable for immune globulin treatment, determining whether immune globulin treatment should be continued, and/or determining if the dose needs to be changed.

BACKGROUND

Immune globulins are sterile preparations of concentrated antibodies derived from pooled plasma of healthy human donors. They can be used in a variety of indications as slow intravenous infusions, repeated at frequencies of every few weeks depending on the indication. Other immune globulin preparations (such as RhIG etc) are used in similar settings and may also be used intramuscularly in situations such as fetomaternal Rh incompatibility.

Immune globulin may be administered for allogeneic bone marrow transplant, chronic lymphocytic leukemia, common variable immunodeficiency, idiopathic thrombocytopenic purpura, pediatric HIV, primary immunodeficiencies, kawasaki disease, chronic inflammatory demyelinating polyneuropathy, and kidney transplant, among other indications.

Sometimes, an immune globulin treatment program may produce side effects, some life-threatening. In some instances, an immune globulin treatment program may begin without side effects, but side effects appear after prolonged or changed treatment. Such failed treatments can be dangerous and expensive.

BRIEF SUMMARY

Described herein are methods for administering immune globulin and devices for use thereof. The methods may generally include measuring a patient's hemolysis levels and determining whether the patient is suitable for immune globulin treatment and/or determining whether immune globulin treatment should be continued. Because hemolysis can be a side-effect (systemic complications, leading to life threatening events such as acute renal failure and disseminated intravascular coagulation) of immune globulin treatment, the methods described herein may advantageously increase the success rate of immune globulin treatments by monitoring hemolysis before and during treatment.

The methods of adjusting immune globulin treatment generally include administering a dose of immune globulin to the patient; monitoring hemolysis in the patient; and adjusting the dose of administered immune globulin based on the monitored hemolysis. Advantageously, monitoring hemolysis and adjusting immune globulin treatments accordingly may reduce the level of harmful hemolysis in the patient. The adjustments may allow a caregiver to continue a treatment safely by reducing a dose of immune globulin, or improve a treatment by safely increasing a dose of immune globulin to increase a therapeutic effect.

In some variations, monitoring the hemolysis in the patient may include obtaining an end-tidal carbon monoxide level from the patient according to a monitoring protocol, and adjusting the dose of administered immune globulin may include adjusting the dose based on the end-tidal carbon monoxide level. Carbon monoxide is produced on a 1:1 molar basis with bilirubin when heme is catabolized. CO levels in the end-tidal component of breath minor those in the blood. Advantageously, end-tidal carbon monoxide monitoring is an accurate, non-invasive way to monitor hemolysis and, therefore, monitor the effects of an immune globulin treatment.

In some variations, the monitoring protocol includes obtaining the end-tidal carbon monoxide level from the patient at a set time after immune globulin administration. Advantageously, this approach can allow a caregiver to detect a hemolysis increase after the patient's body has processed the immune globulin, experienced a hemolysis increase, and passed the resulting carbon monoxide produced to the lungs. In some variations, the set time is about 15 minutes. In some variations, the set time is about 30 minutes and the immune globulin is administered intramuscularly.

In some variations, the monitoring protocol includes obtaining the end-tidal carbon monoxide level from the patient at set intervals during immune globulin administration. In some variations, obtaining the end-tidal carbon monoxide level from the patient at set intervals includes obtaining the end-tidal carbon monoxide level from the patient every hour. The set interval measurement may be used in conjunction with an initial measurement at a set time (see previous paragraph). Once immune globulin treatment has begun and an initial measurement shows no adverse side effects, then less frequent measurements may be sufficient.

In some variations, the monitoring protocol includes obtaining the end-tidal carbon monoxide level from the patient when the dose of administered immune globulin is changed. In some variations, the monitoring protocol includes obtaining the end-tidal carbon monoxide level from the patient after completion of administration of the dose of immune globulin.

In some variations, the monitoring protocol includes obtaining the end-tidal carbon monoxide level from the patient at a set time after completion of the dose of immune globulin administration. In some variations, the set time is about 30 minutes.

In some variations, the end-tidal carbon monoxide level is obtained using a portable breath analyzer.

In some variations, the method includes measuring a baseline end-tidal carbon monoxide level of the patient prior to administration of the dose of immune globulin. In some variations, the adjusting the dose of administered immune globulin includes ending administration of the dose of immune globulin if the end-tidal carbon monoxide level obtained during administration increased by a set amount above the baseline end-tidal carbon monoxide level. In some variations, the set amount is about 0.5 ppm. 0.5 ppm may reflect an increase from a baseline of 1.5 ppm to 2 ppm.

In some variations, obtaining an end-tidal carbon monoxide level from the patient includes: drawing a flow of air from the breath of a patient; monitoring the carbon dioxide level of the flow of air; identifying a point of transition between an increasing carbon dioxide level and a decreasing carbon dioxide level in the flow of air, the point of transition representative of a change from exhalation to inhalation in the breath of the patient; upon identification of the transition point, isolating a sample volume of the flow of air drawn prior to the transition point; diverting a continued flow of air past the isolated sample volume; monitoring the carbon dioxide level of the continued flow of air to confirm the change from exhalation to inhalation in the breath of the patient; upon confirmation of the change from exhalation to inhalation in the breath of the patient, diverting the continued flow of air to displace the isolated sample volume through at least one gas measurement component; and measuring using a gas analyzer, the carbon monoxide level in the isolated sample volume.

In some variations, the method includes measuring a baseline hemolysis level of the patient prior to administration of the dose of immune globulin. In some variations, adjusting the dose of administered immune globulin includes ending administration of the dose of immune globulin if the monitored hemolysis level increases by a set amount above the baseline hemolysis level.

In some variations, the immune globulin is administered intravenously. In some variations, the immune globulin is administered intramuscularly.

In some variations, the dose of immune globulin includes IgG antibodies. In some variations, the dose of immune globulin includes anti-D IgG antibodies.

In some variations, the method is used for an indication selected from the group consisting of allogeneic bone marrow transplant, chronic lymphocytic leukemia, common variable immunodeficiency (CVID), idiopathic thrombocytopenic purpura, pediatric HIV, adult HIV, primary immunodeficiencies, Kawasaki disease, chronic inflammatory demyelinating polyneuropathy (CIDP), kidney transplant, alzheimer's disease, autism, Bechet's disease, capillary leak syndrome, chronic fatigue syndrome, clostridium difficile colitis, dermatomyositis, polymyositis, Grave's ophthalmopathy, Guillain-Barre syndrome, Kimura disease, inclusion body myositis, infertility, Lambert-Eaton syndrome, Lennox-Gastaut, lupus erythematosus, multifocal motor neuropathy, multiple sclerosis, muscular dystrophy, myasthenia gravis, neonatal alloimmune thrombocytopenia, parvovirus B19 infection, pemphigus, post-transfusion purpura, renal transplant rejection, Sjogren's syndrome, stiff person syndrome, Susac's syndrome, opsoclonus myoclonus, sepsis, toxic epidermal necrolysis, and multiple myeloma.

Use of a method of adjusting immune globulin administration may include any of the methods of adjusting immune globulin administration described above.

The methods of selecting a patient for administration of immune globulin generally include: determining a baseline hemolysis level of a patient; in response to determining a high level of hemolysis: forego administering immune globulin to the patient; and in response to determining a low level of hemolysis: administering immune globulin to the patient. Hemolysis may be related to the presence of various comorbid conditions such as the presence of hemolysis at baseline. By measuring hemolysis at baseline, the methods described herein may advantageously rule out unsuitable patients from receiving immune globulin treatment.

In some variations, determining a baseline hemolysis level of the patient includes measuring a baseline end-tidal carbon monoxide level. In some variations, a high level of hemolysis is a baseline end-tidal carbon monoxide level measurement greater than 2 ppm. In some variations, a low level of hemolysis is a baseline end-tidal carbon monoxide level measurement less than 1 ppm.

In some variations, the method may also include determining a moderate level of hemolysis is present, administering immune globulin at a lower dose than if a low level of hemolysis was determined. In some variations, determining a baseline hemolysis level of the patient includes measuring a baseline end-tidal carbon monoxide level, and wherein a moderate level of hemolysis is a baseline end-tidal carbon monoxide level measurement between 1 and 2 ppm.

The methods of selecting a patient for administration of immune globulin may include, after a patient is selected for administration, the methods of adjusting immune globulin administration described above.

Use of a method of selecting a patient for administration of immune globulin may include any of the methods of selecting a patient for administration of immune globulin described above.

DETAILED DESCRIPTION

Described herein are methods for administering immune globulin and devices for use thereof. The methods may generally include measuring a patient's hemolysis levels and determining whether the patient is suitable for immune globulin treatment and/or determining whether immune globulin treatment should be continued. Because hemolysis can be a side-effect (systemic complications, leading to life threatening events such as acute renal failure and disseminated intravascular coagulation) of immune globulin treatment, the methods described herein may advantageously increase the success rate of immune globulin treatments by monitoring hemolysis before and during treatment.

Figure 1:
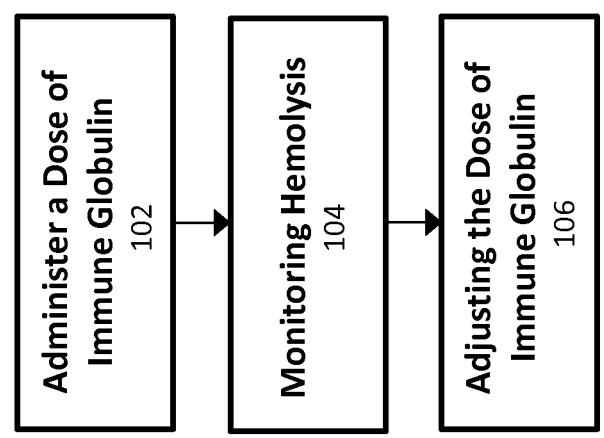
FIG. 1 shows one variation of a method of adjusting immune globulin administration.

FIG. 1 is a flowchart of a method 100 of adjusting immune globulin treatment in accordance with a variation. Method 100 includes administering 102 a dose of immune globulin to a patient, monitoring 104 hemolysis in the patient, and adjusting 106 the dose of administered immune globulin based on the monitored hemolysis. Advantageously, monitoring hemolysis and adjusting immune globulin treatments accordingly may reduce the level of harmful hemolysis in the patient. The adjustments may allow a caregiver to continue a treatment safely by reducing a dose of immune globulin, or improve a treatment by safely increasing a dose of immune globulin to increase a therapeutic effect.

In some variations, monitoring 104 the hemolysis in the patient may include obtaining an end-tidal carbon monoxide level from the patient according to a monitoring protocol, and adjusting the dose of administered immune globulin may include adjusting the dose based on the end-tidal carbon monoxide level. Carbon monoxide is produced on a 1:1 molar basis with bilirubin when heme is catabolized. CO levels in the end-tidal component of breath minor those in the blood. Advantageously, end-tidal carbon monoxide monitoring is an accurate, non-invasive way to monitor hemolysis and, therefore, monitor the effects of an immune globulin treatment.

In some variations, the monitoring protocol includes obtaining the end-tidal carbon monoxide level from the patient at a set time after immune globulin administration. Advantageously, this approach can allow a caregiver to detect a hemolysis increase after the patient's body has processed the immune globulin, experienced a hemolysis increase, and passed that effect to the alveoli in the lungs. In some variations, the set time is about 15 minutes. In some variations, the set time is about 30 minutes and the immune globulin is administered intramuscularly.

In some variations, the monitoring protocol includes obtaining the end-tidal carbon monoxide level from the patient at set intervals during immune globulin administration. In some variations, obtaining the end-tidal carbon monoxide level from the patient at set intervals includes obtaining the end-tidal carbon monoxide level from the patient every hour.

In some variations, the monitoring protocol includes obtaining the end-tidal carbon monoxide level from the patient when the dose of administered immune globulin is changed. In some variations, the monitoring protocol includes obtaining the end-tidal carbon monoxide level from the patient after completion of administration of the dose of immune globulin.

In some variations, the monitoring protocol includes obtaining the end-tidal carbon monoxide level from the patient at a set time after completion of the dose of immune globulin administration. In some variations, the set time is about 30 minutes.

In some variations, the method includes measuring a baseline end-tidal carbon monoxide level of the patient prior to administration of the dose of immune globulin. In some variations, the adjusting the dose of administered immune globulin includes ending administration of the dose of immune globulin if the end-tidal carbon monoxide level obtained during administration increased by a set amount above the baseline end-tidal carbon monoxide level. In some variations, the set amount is about 0.5 ppm.

In some variations, obtaining an end-tidal carbon monoxide level from the patient includes: drawing a flow of air from the breath of a patient; monitoring the carbon dioxide level of the flow of air; identifying a point of transition between an increasing carbon dioxide level and a decreasing carbon dioxide level in the flow of air, the point of transition representative of a change from exhalation to inhalation in the breath of the patient; upon identification of the transition point, isolating a sample volume of the flow of air drawn prior to the transition point; diverting a continued flow of air past the isolated sample volume; monitoring the carbon dioxide level of the continued flow of air to confirm the change from exhalation to inhalation in the breath of the patient; upon confirmation of the change from exhalation to inhalation in the breath of the patient, diverting the continued flow of air to displace the isolated sample volume through at least one gas measurement component; and measuring using a gas analyzer, the carbon monoxide level in the isolated sample volume. Exemplary methods of obtaining an end-tidal volume are described in U.S. Pat. Nos. 9,095,276 and 8,021,308 and U.S. patent application Ser. Nos. 13/722,950, 14/150,625, 14/179,381, 14/473,878, 14/474,019, and 14/664,728, the contents of which are incorporated herein in their entireties.

In some variations, the method includes measuring a baseline hemolysis level of the patient prior to administration of the dose of immune globulin. In some variations, adjusting the dose of administered immune globulin includes ending administration of the dose of immune globulin if the monitored hemolysis level increases by a set amount above the baseline hemolysis level.

In some variations, the immune globulin is administered intravenously. In some variations, the immune globulin is administered intramuscularly.

In some variations, the dose of immune globulin includes IgG antibodies. In some variations, the dose of immune globulin includes anti-D IgG antibodies.

In some variations, the method is used for an indication selected from the group consisting of allogeneic bone marrow transplant, chronic lymphocytic leukemia, common variable immunodeficiency (CVID), idiopathic thrombocytopenic purpura, pediatric HIV, adult HIV, primary immunodeficiencies, Kawasaki disease, chronic inflammatory demyelinating polyneuropathy (CIDP), kidney transplant, alzheimer's disease, autism, Bechet's disease, capillary leak syndrome, chronic fatigue syndrome, clostridium difficile colitis, dermatomyositis, polymyositis, Grave's ophthalmopathy, Guillain-Barre syndrome, Kimura disease, inclusion body myositis, infertility, Lambert-Eaton syndrome, Lennox-Gastaut, lupus erythematosus, multifocal motor neuropathy, multiple sclerosis, muscular dystrophy, myasthenia gravis, neonatal alloimmune thrombocytopenia, parvovirus B19 infection, pemphigus, post-transfusion purpura, renal transplant rejection, Sjogren's syndrome, stiff person syndrome, Susac's syndrome, opsoclonus myoclonus, sepsis, toxic epidermal necrolysis, and multiple myeloma.

In some variations, the end-tidal carbon monoxide level is obtained using a portable breath analyzer. Exemplary portable breath analyzers are described in U.S. application Ser. Nos. 14/179,381, 14/473,878, and 14/474,019, the contents of which are incorporated herein in their entireties. Other breath analyzers could also be used, such as described in U.S. Pat. Nos. 9,095,276 and 8,021,308, the contents of which are incorporated herein in their entireties. The analyzers may send a signal to an immune globulin administration device. The signal may include the end-tidal carbon monoxide level. In other variations, the signal may include whether the end-tidal carbon monoxide level exceeds a threshold. In some variations, the breath analyzer and immune globulin administration device may be an integral device.

Use of a method of adjusting immune globulin administration may include any of the methods of adjusting immune globulin administration described above.

Figure 2:
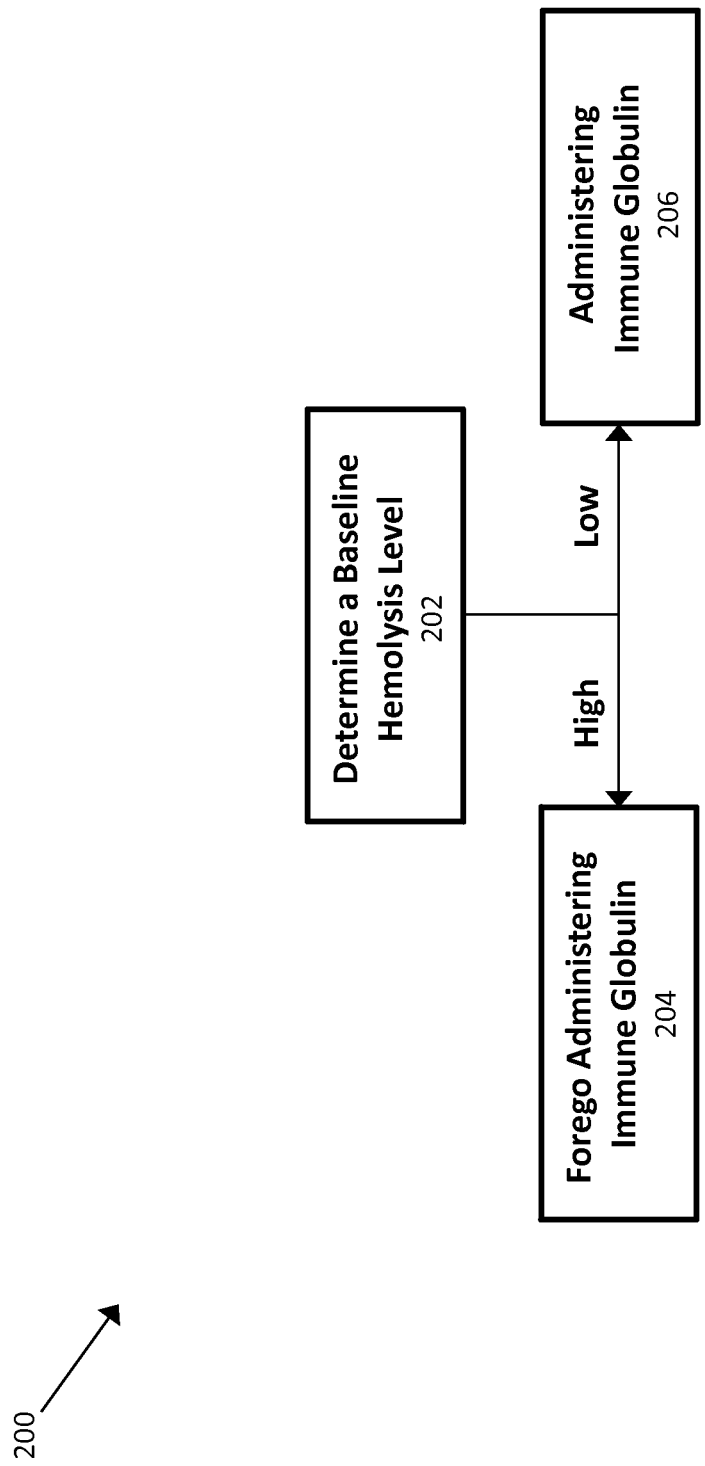
FIG. 2 shows one variation of a method of selecting a patient for administration of immune globulin.

FIG. 2 is a flowchart of a method 200 of selecting a patient for administration of immune globulin. Method 200 includes determining 202 a baseline hemolysis level of a patient; in response to determining a high level of hemolysis: forego administering 204 immune globulin to the patient; and in response to determining a low level of hemolysis: administering 206 immune globulin to the patient. Hemolysis may be related to the presence of various comorbid conditions such as the presence of hemolysis at baseline. By measuring hemolysis at baseline, the methods described herein may advantageously rule out unsuitable patients from receiving immune globulin treatment.

In some variations, determining a baseline hemolysis level of the patient includes measuring a baseline end-tidal carbon monoxide level. In some variations, a high level of hemolysis is a baseline end-tidal carbon monoxide level measurement greater than 2 ppm. In some variations, a low level of hemolysis is a baseline end-tidal carbon monoxide level measurement less than 1 ppm.

In some variations, the method may also include determining a moderate level of hemolysis is present, administering immune globulin at a lower dose than if a low level of hemolysis was determined. In some variations, determining a baseline hemolysis level of the patient includes measuring a baseline end-tidal carbon monoxide level, and wherein a moderate level of hemolysis is a baseline end-tidal carbon monoxide level measurement between 1 and 2 ppm.

The methods of selecting a patient for administration of immune globulin may include, after a patient is selected for administration, the methods of adjusting immune globulin administration described above.

Use of a method of selecting a patient for administration of immune globulin may include any of the methods of selecting a patient for administration of immune globulin described above.

The invention claimed is:

1. A method of adjusting immune globulin administration comprising:
   isolating a sample volume from a breath of the patient using a portable breath analyzer; and
   diverting a continued flow of air to displace the isolated sample volume through a gas measurement component of the portable breath analyzer to measure an end-tidal carbon monoxide level in the isolated sample volume,
   wherein the end-tidal carbon monoxide level determines a hemolysis level of the patient, and
   wherein in response to determining a high level of hemolysis, forego administering immune globulin to the patient, the high level of hemolysis being determined by the end-tidal carbon monoxide level measurement being greater than 2 ppm, and
   wherein in response to determining a low level of hemolysis, administering immune globulin to the patient, the low level of hemolysis being determined by the end-tidal carbon monoxide level measurement being less than 1 ppm.

2. The method of claim 1, further comprising in response to determining a moderate level of hemolysis is present, administering immune globulin at a lower dose than if a low level of hemolysis was determined, wherein the moderate level of hemolysis is an end-tidal carbon monoxide level measurement between 1 and 2 ppm.

* * * * *